United States Patent [19]

Fletcher

[11] Patent Number: 5,044,753
[45] Date of Patent: Sep. 3, 1991

[54] ENVIRONMENTALLY SEALED COLORIMETER FOR INDUSTRIAL ENVIRONMENTS

[75] Inventor: Thomas A. Fletcher, Freeport, Ill.
[73] Assignee: Honeywell Inc., Minneapolis, Minn.
[21] Appl. No.: 541,552
[22] Filed: Jun. 21, 1990
[51] Int. Cl.⁵ .............................................. G01J 3/50
[52] U.S. Cl. .................................. 356/402; 250/226; 364/526; 356/425
[58] Field of Search ............... 356/402, 405, 406, 407, 356/409, 410, 411, 425; 364/526; 250/226

[56] References Cited

U.S. PATENT DOCUMENTS 3,935,436 1/1976 Holschlag et al. .................. 356/244
3,941,487 3/1976 Ehret et al. .......................... 356/411
4,849,625 7/1989 Camerini Porzi .................... 356/425

Primary Examiner—F. L. Evans
Attorney, Agent, or Firm—Robert B. Leonard

[57] ABSTRACT

A colorimeter for characterizing the color of an object is placed in an environmentally sealed enclosure for use in industrial environments. In order to maintain an acceptable operating temperature for the colorimeter's electronics and lamp, a heat shield is placed around the lamp to substantially isolate it from the electronics. The heat shield and the environmentally sealed enclosure are made of a highly heat conductive material such as aluminum. The heat shield is thermally coupled to the environmentally sealed enclosure.

9 Claims, 2 Drawing Sheets 5,044,753

ENVIRONMENTALLY SEALED COLORIMETER FOR INDUSTRIAL ENVIRONMENTS

BACKGROUND OF THE INVENTION

This invention is directed toward the field of colorimeters, and more specifically to colorimeters sealed in environmentally tight enclosures.

Colorimeters are well known devices used to characterize the color of an object and compare it to the color of other objects. The colorimeter provides illumination which is reflected or transmitted by the object and is transmitted optically to a dispersing element which disperses the coherent light spectrally. A detector array converts the spectra of the light into discrete signals which provide a color signature of the object. The signal is then sent to an A/D converter and then input into a microprocessor for processing. After the color signature has been generated by the detector array it may then be compared to signatures stored in memory.

There was a desire among some users of colorimeters to use the devices in industrial environments. Such use would expose a colorimeter to airborne dust and moisture, and occasionally to hose directed water. However, due to the nature of the colorimeter's components, such an environment would cause colorimeters to fail.

Yet, merely enclosing a colorimeter in an environmentally tight enclosure is not a complete solution to the problem. Both the National Electrical Manufacturers Association (NEMA) and Underwriter's Laboratory (UL) have issued standards which require that the external surface temperature of such a device be no greater than 70 degrees C., with an external ambient of 40 degrees C. Both the lighting means and the processing electronics radiate heat, at least some of which must be dispersed to meet the NEMA and UL standards.

Further, halogen lamps, which were often used as the source of illumination, have a regenerative cycle which is dependent upon the temperature of the surrounding air. Such a halogen lamp must be kept at a constant preselected temperature in order to maximize lamp life.

Thus, it is an object of the present invention to provide a colorimeter which is environmentally sealed from the surrounding environment while still allowing for cooling of the processing electronics and lighting means.

SUMMARY OF THE INVENTION

The present invention is an environmentally sealed colorimeter which provides heat dissipation path for internal heat sources. The colorimeter includes an enclosure with an access hole and light entry and exit ports, a cover for sealing the access hole, processing electronics mounted in the enclosure, a lighting means for illuminating an object being scanned and a heat shield for shielding the lighting means from the processing electronics and to provide a heat dissipation path for heat generated by the lighting means.

DETAILED DESCRIPTION OF THE PREFERRED EMBODIMENT

Figure 1:
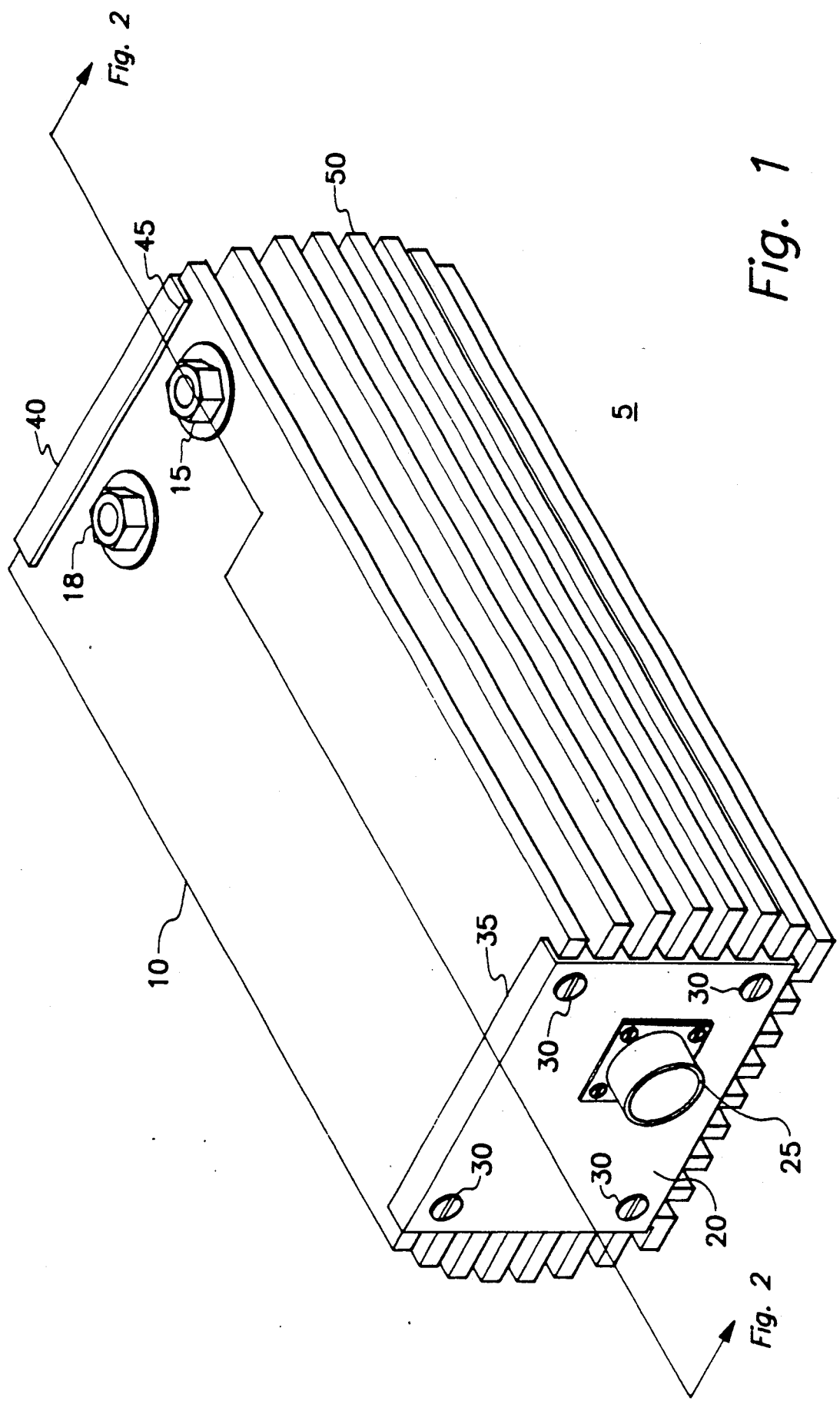
FIG. 1 is a perspective view of the external housing of the inventive colorimeter.
Figure 2:
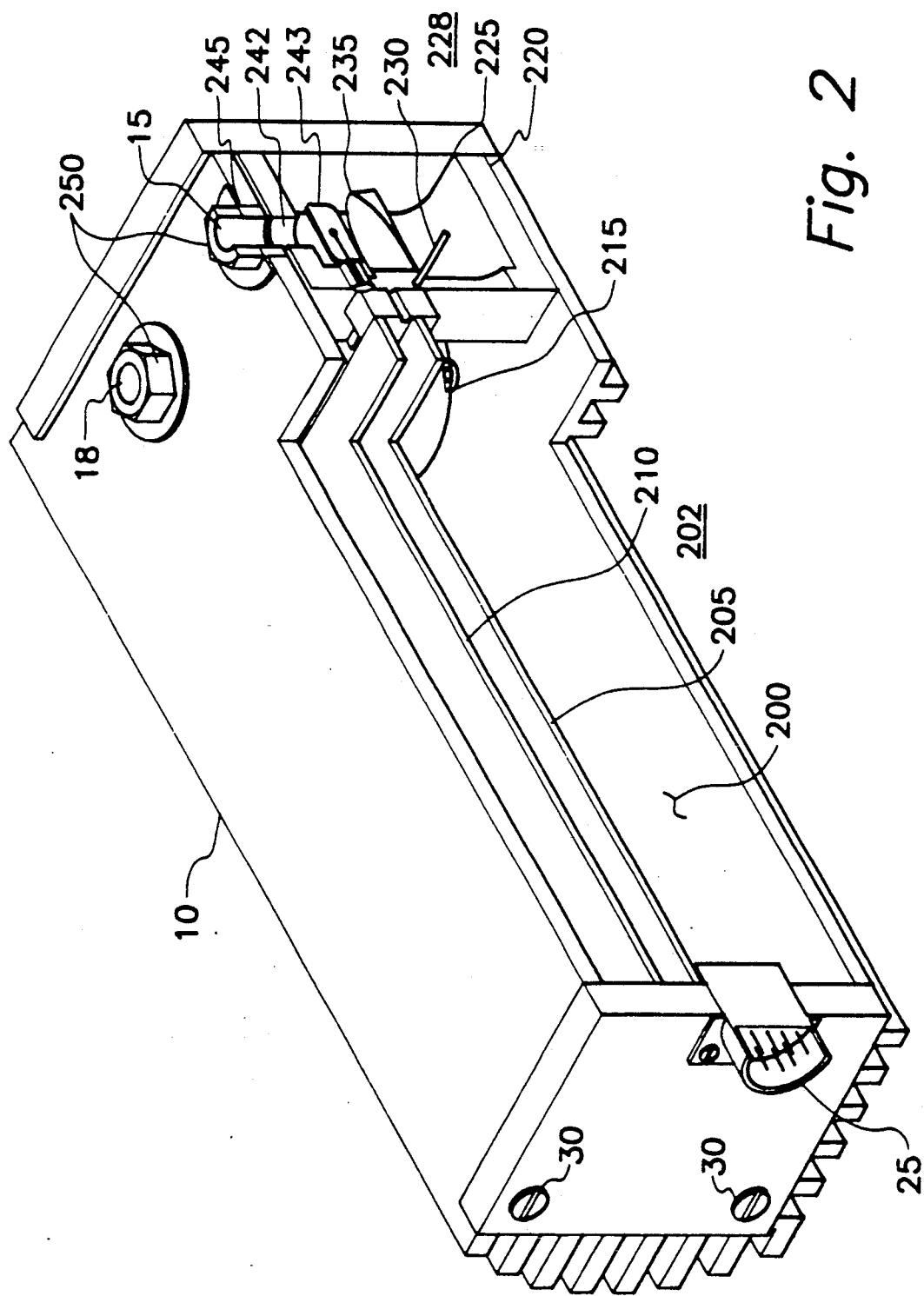
FIG. 2 is a cutaway view taken along line 2—2, of the colorimeter of FIG. 1.

The following description, which corresponds with FIGS. 1 and 2, will allow one of ordinary skill in the art to build and use the inventive colorimeter.

Referring to FIG. 1, thereshown is the colorimeter 5 of the present invention. Housing or enclosure 10 is constructed of a material with good heat transfer characteristics. One material particularly well suited to such a use based on heat transfer, extrudability and cost is type 6061-T6 aluminum. Enclosure 10 includes an internal cavity 200, shown in FIG. 2. Internal cavity 200 is adapted to hold internal circuit parts (see FIG. 2).

Light exit port 15, is formed in enclosure 10 so that light from an internal lighting means (see FIG. 2) can be directed at an object (not shown) to be scanned. Light entry port 18, is formed in enclosure 10 so that light transmitted or reflected by the object can be presented to a processing means (see FIG. 2) for analysis.

Internal cavity 200 can be sealed from the environment surrounding the colorimeter 5 through the use of covers 20, 40. Screws 30 are used to hold the covers 20, 40 in place. Elastomer seals 35, 45 are interposed between covers 20, 40 and enclosure 10 to insure that an environmental seal is created.

In order to allow for external cable connections to the internal circuit parts, a cable connector 25 is mounts on and penetrates cover 20. An elastomer seal (not shown) is interposed between the cable connector and the cover 20 to ensure an environmentally tight seal.

Turning now to FIG. 2, thereshown is a cutaway view of the colorimeter 5 of FIG. 1. As can be seen, enclosure 10 defines an internal cavity 200. Internal cavity 200 holds a data processing means 202 including power supply 205 and processor 210, lighting means 228 including lamp extractor 230, concave mirror 235, lamp 240, heat shield 220, and detector optics means 215.

At this point, a brief description of the operation of the colorimeter is in order. Light from lamp 240 travels through a hole 242 in heat shield 220 into light exit port 15. Light exit port 15 will be attached to an optical fiber (not shown) in actual use. The end of the optical fiber not inserted into light exit port 15 will be placed near an object to be scanned. A second optical fiber will have one end positioned near the object being scanned, the other end of the optical fiber being inserted in light entry port 18. Light from lamp 240 travels to the object along the first optical fiber, is reflected or transmitted by the object onto the second optical fiber and returned to the detector optics means 215. The detector optics means 215 breaks the coherent light received from the object into an array of signals representative of the intensity of groups of wavelengths present in the coherent light. The processor 210 then compares the sensed array of signals with one or more stored arrays of signals to determine the color signature of the scanned object.

When energized, both the processing means 202 and the lighting means 228 produce enough heat that damage may result to the internal circuitry if some cooling means is not provided. Because of the desirability of having the colorimeter sealed from its environment and due to the cost of using forced air, the colorimeter cannot be cooled by forcing air through the internal cavity. Thus, only natural convection cooling is available as a cooling method. Here, the enclosure is designed to have sufficient surface area to disperse the internally produced heat. The surface area is increased by adding one or more fins 50 to the exterior of enclosure 10. The amount of surface area required to disperse a known quantity of internally generated heat is calculated using a method well known in the art.

To further aid in protecting the processing means from excessive heat, a heat shield 220 is interposed between lamp 240 and processing means 202. In the present embodiment, heat shield 220 takes the shape of a rectangular parallelepiped having a hollow internal cavity and one missing side. The missing side is arranged so that when cover 40 is in place on enclosure 10, lamp 240 is substantially isolated from the internal circuitry. Heat shield 220 is adapted to provide a heat conduction path from the lamp 240 to the external environment. In the present embodiment, heat shield 240 is constructed of a highly heat conductive material such as aluminum type 2024-T6, and the heat shield is arranged so that a portion of the heat shield contacts an inner wall of internal cavity 200.

In order to reduce the heat produced by the colorimeter, the present lighting means was created. Concave mirror 235 collects and focuses light which would otherwise be wasted, onto an optical fiber inserted into the light exit port to increase the light presented to the object to be scanned. Use of the mirror in turn allows for a smaller lamp to be used to illuminate an object with a desired amount of light, thus reducing the heat produced over a colorimeter not using a mirror as shown.

By using the above arrangement, the NEMA and UL standards may be maintained. Further, the air temperature of the air surrounding the lamp may be maintained at a level which allows the regenerative cycle of the lamp to operate. Note that the amount of surface area of the enclosure will vary with, among other things, lamp heat output and the amount of internal circuitry.

It should be noted that many access holes may be made in enclosure 10, but that there should be a cover for each hole, each cover providing for some means for sealing the internal cavity 200 from the external environment during operation of the colorimeter. Further, in order to seal the light exit and entry ports 15, 18 from the environment, threaded couplings 250 are inserted into the ports, with elastomer seals 245 being interposed between the couplings and enclosure 10. In order to operably seal the light exit and entry ports, optical fibers are inserted into the threaded couplings, and a packing nut is tightened onto the threads. An elastomer O ring is contained inside each of the threaded couplings, and surrounds an optical fiber inserted therein to provide sealing around the optical fibers.

The foregoing has been a description of a novel and non-obvious environmentally sealed colorimeter. The applicant does not intend to limit the invention by the foregoing description, but instead defines the limit of the invention in the claims appended hereto.

I claim:

1. An environmentally sealed colorimeter for characterizing the color of an object, comprising:
    lighting means for illuminating the object;
    detector optics means for receiving light from the illuminated object and to produce an object color signature;
    data processing means for receiving said object color signature and to compare it with stored color signatures;
    an enclosure having an opening therein and light entry and exit ports, said enclosure housing said data processing means and said lighting means;
    a heat shield which substantially surrounds said lighting means having a first light port formed therein, said heat shield being comprised of a thermally conductive material and being thermally coupled to said enclosure; and
    a cover having sealing means, said cover mountable on said enclosure to seal said opening.

2. The colorimeter of claim 1, wherein said lighting means comprises:
    a lamp and a mirror, said lamp being positioned between said mirror and said first light port, said mirror focusing light on said light port.

3. The colorimeter of claim 2, wherein said light entry and exit ports are comprised of optical fiber connectors receiving an optical fiber, said light entry port being positioned such that an optical fiber may pass therethrough and receive light from said first light port, said optical fiber connectors when connected to an optical fiber forming an environmental seal preventing outside contaminants from entering the colorimeter therethrough.

4. The colorimeter of claim 3, wherein said heat shield is formed of type 2024-T6 aluminum and said enclosure is formed of type 6061-T6 aluminum.

5. The colorimeter of claim 1, wherein said enclosure further comprises:
    cooling fins located on an exterior side of said enclosure, said cooling fins aiding in cooling of the colorimeter.

6. The colorimeter of claim 5, wherein said lighting means comprises:
    a lamp and a mirror, said lamp being positioned between said mirror and said first light port, said mirror focusing light on said light port.

7. The colorimeter of claim 6, wherein said light entry and exit ports are comprised of optical fiber connectors for receiving an optical fiber, said light entry port being positioned such that an optical fiber may pass therethrough and receive light from said first light port, said optical fiber connectors when connected to an optical fiber forming an environmental seal preventing outside contaminants from entering the colorimeter therethrough.

8. The colorimeter of claim 7, wherein said heat shield is formed of type 2024-T6 aluminum and said enclosure is formed of type 6061-T6 aluminum.

9. An improved colorimeter of the type including lighting means for illuminating an object, a detector optics means for receiving light from the object and producing an object color signature therefrom and processing means for comparing the object color signature with stored color signatures, wherein the improvement comprises:
    an enclosure having an access hole and cover and light entry and exit ports, said enclosure housing the lighting and processing means, said cover mounting over and environmentally seal said access hole; and
    a heat shield which substantially surrounds said lighting means having a light port formed therein, said heat shield being comprised of a thermally conductive material and being thermally coupled to said enclosure.

* * * * *